United States Patent
Nishioka et al.

[11] Patent Number: 5,861,173
[45] Date of Patent: Jan. 19, 1999

[54] LONG-LASTING RELEASE NIFEDIPINE PREPARATION

[75] Inventors: Takaaki Nishioka, Nabari; Kenji Kuratani; Haruo Kanasaki, both of Shiga, all of Japan; Helmut Luchtenberg, Niederkassel, Germany; Ulrich Tenter, Solingen, Germany; Andreas Ohm, Neuss, Germany

[73] Assignee: Bayer Aktiengesellschaft, Leverkusen, Germany

[21] Appl. No.: 755,381

[22] Filed: Nov. 21, 1996

[30] Foreign Application Priority Data

Nov. 28, 1995 [JP] Japan .................. 7-331217

[51] Int. Cl.⁶ .................. A61K 9/32; A61K 9/36
[52] U.S. Cl. .................. 424/480; 424/482; 424/474
[58] Field of Search .................. 424/474, 479, 424/480, 482, 464, 465

[56] References Cited

U.S. PATENT DOCUMENTS

| | | | |
|---|---|---|---|
| 4,892,741 | 1/1990 | Ohm et al. | 424/479 |
| 4,933,186 | 6/1990 | Ohm et al. | 424/476 |
| 4,966,772 | 10/1990 | Ohm et al. | 424/482 |

FOREIGN PATENT DOCUMENTS

| | | |
|---|---|---|
| 299211 | 1/1989 | European Pat. Off. . |
| 306699 | 3/1989 | European Pat. Off. . |
| 339420 | 11/1989 | European Pat. Off. . |
| 387782 | 9/1990 | European Pat. Off. . |

OTHER PUBLICATIONS

English language abstract of JP 40–14446 (1984).
English language abstract of JP 04–11699 (1994).

Primary Examiner—Thurman K. Page
Assistant Examiner—James M. Spear
Attorney, Agent, or Firm—Sprung Kramer Schaefer & Briscoe

[57] ABSTRACT

This invention provides a long-lasting release solid nifedipine preparation which exhibits clinically sufficient effect when administered once per day. A press coated tablet whose core and shell each contains nifedipine, the dissolution rate of nifedipine from said tablet being (a) in the dissolution test using a sinker according to method 2 of the dissolution test method as prescribed by the Pharmacopoeia of Japan, after 2 hours 10–40% after 4 hours 30–65% after 6 hours at least 55%, and (b) in the dissolution test according to the disintegration test method as prescribed by the Pharmacopoeia of Japan, after 3 hours 20–45% after 4 hours 30–65%.

12 Claims, 2 Drawing Sheets

Dissolution Test by Method 2 (using sinker) of the Pharmacopoeia of Japan

—●— Example 1  —■— Example 2
—△— Comparative Example 1  —◇— Comparative Example 2
—*— Comparative Example 3

LONG-LASTING RELEASE NIFEDIPINE PREPARATION

[FIELD OF INDUSTRIAL UTILIZATION]

This invention relates to a long-lasting release nifedipine solid preparation. More specifically, the invention relates to a long-lasting release nifedipine-containing press coated tablet which can exhibit clinically sufficiently significant antihypertensive action by single time administration per day.

[CONVENTIONAL TECHNOLOGY AND PROBLEMS]

In the past, a nifedipine-containing tablet which contains nifedipine crystals of a specific surface area and pharmaceutically acceptable, inert adjuvant has been proposed as a long acting, solid preparation of nifedipine (Japanese Patent Publication No. 14446/1984). This tablet, however, requires administration of twice per day for exhibiting sufficiently useful effect for clinical purpose.

In treating hypertensive patients or the like, which treatment must be given over a relatively prolonged period, plural times medication per day is not only cumbersome, but also liable to cause problems such as that patients may forget to take the medicine or may take it at irregular intervals, whereby jeopardizing sure and safe therapy. For this reason, development of a preparation of nifedipine, a treating agent of hypertension, which exhibits clinically fully useful effect by single time administration per day ("once-a-day tablet") has heretofore been strongly demanded.

As a preparation which meets such demands, Japanese Patent Publication No. 11699/1994 discloses a solid nifedipine preparation composed of a core containing nifedipine in rapid release form and a coating containing nifedipine in sustained release form. In this solid preparation, a hydrophilic gel-forming polymer is used to allow the coating sustained release.

The object of the present invention is to provide a nifedipine preparation which maintains effective plasmic concentration of nifedipine over many hours (normally 24 hours or more) and exhibits clinically sufficient effect by single time administration per day.

Other object of the present invention is to provide a nifedipine preparation which is less sensitive to mechanical agitation and stress conditions to minimize undesired interactions with food and agitation dependencies.

Further object of the present invention is to provide a nifedipine preparation which is also to show a high bioavailability in spite of the slow release core, and to maintain high effective plasmic concentration of nifedipine over a long period, preferably over at least 24 hours.

[Means to solve the problems]

With the view to accomplish the above object, we have made extensive studies on the sustained release press coated tablet like the one disclosed in said Patent Publication No. 11699/1994, whose core and the shell coating said core each contains nifedipine, and discovered that the object can be realized by giving the core an erodible matrix structure containing nifedipine and a hydrophilic gel-forming high molecular weight substance, and giving the shell an erodible matrix structure containing, in addition to nifedipine and a hydrophilic gel-forming high molecular weight substance, a disintegration suppression substance. Whereupon the present invention is completed.

Thus, the invention provides a nifedipine-containing press coated tablet which comprises a core containing nifedipine and hydrophilic gel-forming high molecular weight substance and a shell which coats the core and which contains nifedipine, hydrophilic gel-forming high molecular weight substance and a disintegration suppression substance, which is characterized in that the dissolution rate of the nifedipine from said tablet is:

(a) in the dissolution test using a sinker according to method 2 of the dissolution test method as prescribed by the Pharmacopoeia of Japan,
after 2 hours 10–40%
after 4 hours 30–65%
after 6 hours at least 55%, and (b) in the dissolution test according to the disintegration test method as prescribed by the Pharmacopoeia of Japan,
after 3 hours 20–45%
after 4 hours 30–65%.

Compared with the aforementioned preparation disclosed in Japanese Patent Publication No. 11699/1994, the major characteristics of the tablet of the present invention is that the coat contains a disintegration suppression substance and the core shows a slower release of nifedipine.

Hereinafter the tablet of the present invention is explained in further details.

The tablet of the present invention is a press coated tablet composed of a core and a shell coating said core. The core contains nifedipine and hydrophilic gel-forming high molecular weight substance. Said hydrophilic gel-forming high molecular weight substance which is blended in the core swells upon contact with water and forms gel, examples of which including cellulose derivatives such as methylcellulose, hydroxypropylcellulose (HPC), hydroxypropylmethylcellulose (HPMC), sodium carboxymethylcellulose; and polyvinyl alcohol. Of those, hydroxy-lower alkylethers of cellulose, particularly hydroxypropylcellulose (HPC), are preferred. Here the term, "lower" signifies that the carbon number is not more than 6. As the HPC, various HPCs of different viscosity levels, e.g., low viscosity HPC (HPC-L) having a viscosity of about 6—about 10 cp, medium viscosity HPC (HPC-M) having a viscosity of about 150–400 cp, and high viscosity HPC having a viscosity of about 1,000—about 4,000 cp, said viscosity values being determined of 2% aqueous solutions thereof at 20° C., can be used. Generally, tendencies are observed that use of high-viscosity HPC lowers the release rate of the active ingredient from the preparation, while use of low-viscosity HPC increases the release rate. Accordingly, by suitably selecting and combining such HPCs of different viscosity levels, release profile of nifedipine from the core can be adjusted.

The core can contain such a hydrophilic gel-forming high molecular weight substance, in general terms by 5–90%, preferably 10–80%, inter alia, 10–70%, the percentages being by weight, based on the total core weight.

Besides the hydrophilic gel-forming high molecular weight substance, the core may further contain, as individual occasion demands, for example, excipients such as starch, e.g., corn starch, potato starch, α-starch, starch, dextrin, carboxymethyl starch, etc.; sugar such as lactose, sucrose, glucose, mannitol, sorbitol, etc.; inorganic salts such as light silicic anhydride, synthetic aluminum silicate, magnesium metasilicate aluminate, calcium phosphate, calcium carbonate, etc.; oils and fats such as paraffin, wax, higher fatty acid, etc.; and cellulosic substances: disintegration agents such as starch, crosscarmellose sodium, carboxymethylstarch sodium, carboxymethylcellulose, calcium carboxymethylcellulose, low substituted hydroxypropylcellulose, crystalline cellulose, crosslinked polyvinylpyrrolidone, etc.: lubricants such as magnesium stearate, talc, synthetic aluminum silicate, etc.: coloring agents such as various food colors: and dissolution promoters such as various surfactants.

In order to meet the purpose of once-a-day tablet as set forth in the present invention, it is desirable to adjust the final composition of the core such that the dissolution rate of nifedipine from a tablet of identical composition with that of the core, as tested according to method 2 of the dissolution test method not using a sinker, as prescribed in the Pharmacopoeia of Japan [hereafter referred to as "Pharmacopoeia method 2 dissolution test (not using sinker)"] is, in general terms:

after 45 minutes 20–70%, preferably 25–65%, more preferably 30–60% after 2 hours at least 65%, preferably at least 70%, more preferably at least 75%.

Here the Pharmacopoeia method 2 dissolution test (not using sinker) is conducted under the following conditions.

Test liquid: phosphoric acid buffer solution at pH 6.8, containing 1% of sodium lauryl sulfate 900 ml Temperature: 37° C.

Rotation rate: 75 rpm.

The tablet having the identical composition with that of the core, which is to be used in the above dissolution test, is compressed under the same conditions employed for compressing the core of the press coated tablet of the present invention.

The prominent feature that characterizes the shell according to the present invention is that it contains, in addition to nifedipine and a hydrophilic gel-forming high molecular weight substance, a disintegration suppression substance. The disintegration suppression substance is a pharmaceutically acceptable, pharmacologically inactive substance which can form a pH-independent matrix together with the said nifedipine and the hydrophilic gel-forming high molecular weight substance, and give robustness to the shell so that the shell disintegrates gradually and stably under mechanically stressful atmosphere such as in the digestive tract. As examples of such disintegration suppression substance, specific pH-independent water-insoluble polymers which are usually used as bases or films for sustained release formulations can be given. Preferably, water-insoluble methacrylate copolymers and water-insoluble cellulose derivatives such as ethylcellulose and cellulose acetate can be used. Of those, an poly(ethyl acrylate, methyl methacrylate, trimethylammonioethyl methacrylate chloride) (hereafter referred to as "aminoalkyl methacrylate copolymer") composed of the three recurring units as indicated by the following formulae (I), (II) and (III):

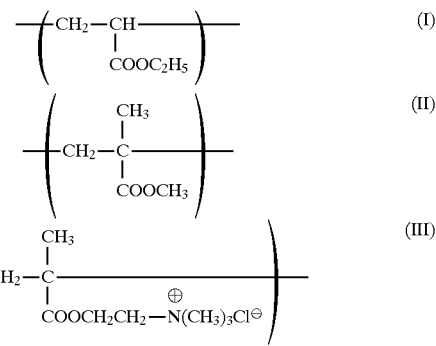

is most preferred.

As said aminoalkyl methacrylate copolymer, one in which the weight ratio of the recurring units of above formulae (I), (II) and (III), i.e., (I)/(II)/(III), is within a range ½/0.1–0.2 is preferred, which also preferably has a viscosity of from about 1 to about 4 centistokes. Such aminoalkyl methacrylate copolymer has been marketed, available under tradenames of Eudragit RS or RL (manufactured by Roehm Pharma G.m.b.H., Germany).

The shell contains such a disintegration suppression substance, in an amount of normally 5–50% by weight, preferably 7.5–40% by weight, more preferably 10–30% by weight, based on the weight of the shell.

As the hydrophilic gel-forming high molecular weight substance to be blended into the shell, those which are named as examples of hydrophilic gel-forming substance to be blended in the core may be named, which can be suitably selected taking into consideration, e.g., the medicine releasability desired of the shell.

The shell can contain such a hydrophilic gel-forming high molecular weight substance normally in a range of 30–90% by weight, preferably 35–85% by weight, more preferably 40–80% by weight, based on the weight of the shell.

The shell may contain, besides nifedipine, a hydrophilic gel-forming high molecular weight substance and a disintegration suppression substance, if necessary, e.g., excipients such as starch, e.g., corn starch, potato starch, α-starch, dextrin, carboxymethyl starch, etc.; sugar such as lactose, sucrose, glucose, mannitol, sorbitol, etc.; inorganic salts such as light silicic anhydride, synthetic aluminum silicate, magnesium metasilicate aluminate, calcium phosphate, calcium carbonate, etc.; oils and fats such as paraffin, wax, higher fatty acid, etc.; and cellulosic substances: disintegrating agents such as starch, crosscarmellose sodium, carboxymethylstarch sodium, carboxymethylcellulose, carboxymethycellulose calcium, low substituted hydroxypropylcellulose, crystalline cellulose, crosslinked, polyvinylpyrrolidone, etc.: lubricants such as magnesium stearate, talc, synthetic aluminum silicate, etc.: coloring agents such as various food colors: and dissolution promoters such as various surfactants.

The final composition of the shell is desirably so adjusted that the dissolution rate of nifedipine from a tablet of identical composition with that of the shell is:

(a) in the dissolution test using a sinker according to method 2 of the dissolution test method as prescribed by the Pharmacopoeia of Japan [hereafter "Pharmacopoeia method 2 dissolution test (using sinker)"], after 2 hours 20–50%, preferably 25–45%, more preferably 30–40%, after 4 hours 40–90%, preferably 45–85%, more preferably 50–80%, after 6 hours at least 75%, preferably at least 80%, more preferably at least 85%, and (b) in the dissolution test according to the disintegration test method as prescribed by the Pharmacopoeia of Japan [hereafter "Pharmacopoeia disintegration test device method"], after 3 hours 30–60%, preferably 35–55%, more preferably 40–50%, after 4 hours 40–90%, preferably 45–85%, more preferably 50–80%.

In the present specification, the Pharmacopoeia method 2 dissolution test (using sinker) is conducted under the following conditions.

Test liquid: phosphoric acid buffer solution at pH 6.8, containing 1% of sodium lauryl sulfate 900 ml Temperature: 37° C.

Rotation rate: 100 rpm

Fixed position of the sinker: fixed at a position at the center between the test liquid level and the upper edge of the stirring blade, and spaced from the container wall by 10 mm, with acid-resistant wire of the diameter not more than 1.0 mm.

Also the Pharmacopoeia disintegration test device method is conducted under the following conditions.

Test liquid: phosphoric acid buffer solution at pH 6.8, containing 1% of sodium lauryl sulfate 900 ml Temperature: 37° C.

An auxiliary disc is used.

The tablet having the identical composition with that of the shell, which is to be used in the above dissolution tests, is compressed under the same conditions as employed for compressing the press coated tablet of the present invention but without using the core.

The press coated tablet of the present invention composed of the core and shell each having the above-described components and composition, can be prepared by, for example, forming a nucleus tablet to serve as the core by an itself known means, and then coating said core tablet with the shell having the above-described composition, using a dry coating machine (press coater).

The compressing conditions in that occasion are not strictly limited, but are variable depending on the dissolution characteristics, etc., desired of the finished tablets. Whereas, normally adequate compressing pressure for the nucleus tablet (core) ranges approximately 0.1–1 ton, and that for the press coated tablets is approximately 0.5–2 tons.

The diameter of the core (the nucleus tablet) is generally within a range of 3–7 mm, and it is desirable that diameter of the finished press coated tablet (uncoated) be normally in the range of 7–12 mm.

The inner nucleus tablet (core) may be applied with a thin film coating preceding the coating with the shell. As the base for such film coating, for example, cellulosic water-soluble coating bases such as HPC, HPMC, hydroxyethyl cellulose, methylhydroxyethyl cellulose, etc.; cellulosic enteric coating bases such as hydroxypropylmethylcellulose phthalate, hydroxypropylmethylcellulose acetate succinate, carboxymethylethyl cellulose, cellulose acetate phthalate, etc.; and enteric film coating bases such as methacrylic acid copolymers, shellac and the like may be named.

Furthermore, the finished tablet may be integrated with at least one layer of light-shielding film coating. As such light-shielding film coating, for example, cellulosic water-soluble coating blended with an adequate amount of a light-shielding agent, e.g., iron sesquioxide and/or titanium dioxide, may be named. As the cellulosic water-soluble coating, HPMC is particularly preferred because of its good film-forming property, such HPMC whose 2% aqueous solution has a viscosity not higher than 100 cp, in particular, not higher than 15 cp, at 20° C. being especially preferred. These film coating base may be added with a plasticizing agent, if necessary, such as polyethylene glycol or the like.

Thus prepared press coated tablets of the subject invention exhibit the following nifedipine dissolution characteristics. Namely, the dissolution rate of nifedipine from the press coated tablet shows a dissolution pattern (profile) of:

(a) according to the Pharmacopoeia method 2 dissolution test (using sinker);
  after 2 hours 10–40%, preferably 15–35%, more preferably 20–29%,
  after 4 hours 30–65%, preferably 35–60%, more preferably 39–56%,
  after 6 hours at least 55%, preferably at least 60%, more preferably at least 65%, and (b) according to the Pharmacopoeia disintegration test device method,
  after 3 hours 20–45%, preferably 25–40%, more preferably 28–35%,
  after 4 hours 30–65%, preferably 35–60%, more preferably 40–55%.

The press coated tablet of the present invention can generally contain 10–120 mg, preferably 20–90 mg, of nifedipine per tablet. The relative ratio of nifedipine contents in the core and shell is not strictly limited, while in general terms the weight ratio of nifedipine content of the core/nifedipine content of shell may be within the range 1/7–3/1, in particular, 1/5–2/1.

The properties of nifedipine which is to be blended and dispersed in the tablets of the present invention are not particularly limited. Normally, however, nifedipine crystals which are micro-pulverized to such a level that their median diameter as measured by sedimentation method or laser diffraction scattering-type particle size distribution method is about 1–30 $\mu$m; or the specific surface area as measured by gas adsorption method is about 0.5–10 $m^2/g$, are conveniently used. Nifedipine which has been made amorphous together with polyvinylpyrrolidone or the like, or nifedipine once dissolved in an organic solvent and thereafter adsorbed onto a porous substance such as light silicic anhydride or the like, may also be used.

Because the press coated tablet of the present invention has the above-described structure, when orally administered, it absorbs digestive fluid or water at the upper part of the digestive tract and its shell forms erodible matrix, but due to its mechanical strength it does not readily collapse under peristaltic motion of the digestive tract and changes into gel from outside surely and slowly. Thus, as the time passes the shell stably and continuously releases nifedipine from the surface thereof. In consequence, at about the time the drug release from the matrix layer of the shell is completed, the preparation reaches the lower digestive tract of low water content, and the core starts to release the drug.

Accordingly, the tablet of the present invention improves the stability against high peristaltic/mechanical agitation of the digestive tract and achieves the excellent effect of maintaining the effective plasmic concentration of nifedipine by administration once per day.

[EXAMPLES]

Hereafter the invention is more specifically explained, referring to the working Examples, in which "Eudragit RSPOL" is a commercial name of a product of Roehm Pharma GmbH of Germany, a poly(ethyl acrylate, methyl methacrylate, trimethylammonioethyl methacrylate chloride).

As HPC-L and HPC-M, those hydroxypropylcellulose products manufactured by Nippon Soda K.K., which respectively have a viscosity of 6.0–10.0 cp (2% aqueous solution, 20° C.) and that of 150–400 cp (2% aqueous solution, 20° C.) were used. As HPMC, hydroxypropylmethylcellulose 2910 manufactured by Shin-etsu Kagaku Kogyo K.K., having a viscosity of 15 cp (2% aqueous solution, 20° C.) was used.

Example 1

Nifedipine 7.0 g (micropulverized crystals)

Lactose 16.4 g

HPC-L 21.4 g

The above starting materials were homogeneously mixed, granulated, dried and sieved, to which 0.2 g of magnesium stearate was added and mixed. The mixture was pressed under a pressure of 0.5 ton with a single punch tableting machine (Korsch EKO), to form the core tablets weighing 45 mg per tablet (diameter=5 mm, thickness=2 mm).

Nifedipine 33.0 g (micropulverized crystals)

HPC-L 116.7 g

HPC-M 49.0 g

Eudragit RSPOL 50.0 g

The above starting materials were homogeneously mixed, granulated, dried and sieved. Then 1.3 g of magnesium stearate was added thereto and mixed. The resulting composition was made the shell which, together with the previously prepared core tablet, was compressed under a pressure of 1 ton with a press coating machine (Kikusui Cleanpress Correct 18DC), to provide press coated tablets containing 40 mg of nifedipine and weighing 295 mg per tablet (diameter=9 mm, thickness=5 mm).

Furthermore, a film coating composed of:

HPMC (15 cp) 3.0 mg polyethylene glycol 4000 1.0 mg iron sesquioxide 1.0 mg was applied onto the tablet, to render the total weight of the final tablet 300 mg.

Example 2

Nifedipine 15.0 g (micropulverized crystals)

Lactose 24.1 g

HPC-L 5.7 g

The above starting materials were homogeneously mixed, granulated, dried and sieved, to which 0.2 g of magnesium stearate was added and mixed. The mixture was compressed under a pressure of 0.5 ton with a single punch tableting machine (Korsch EKO), to form the core tablets weighing 45 mg per tablet (diameter=5 mm, thickness=2 mm).

Nifedipine 25.0 g (micropulverized crystals)

HPC-L 124.7 g

HPC-M 49.0 g

Eudragit RSPOL 50.0 g

The above starting materials were homogeneously mixed, granulated, dried, sieved and mixed with 1.3 g of magnesium stearate. The resulting composition was made the shell which, together with the previously prepared core tablet, was compressed under a pressure of 1 ton with a press coating machine (Kikusui Cleanpress Correct 18DC), to provide press coated tablets containing 40 mg of nifedipine and weighing 295 mg per tablet (diameter=9 mm, thickness=5 mm). The tablets were further applied with the film coating same to that used in Example 1.

Example 3

Nifedipine 7.5 g (micropulverized crystals)

Lactose 20.3 g

HPC-L 17.0 g

The above starting materials were homogeneously mixed, granulated, dried, sieved and then mixed with 0.2 g of magnesium stearate. The mixture was compressed under a pressure of 0.5 ton with a single punch tableting machine (Korsch EKO), to form the core tablets weighing 45 mg per tablet (diameter=5 mm, thickness=2 mm).

Nifedipine 12.5 g (micropulverized crystals)

HPC-L 141.2 g

HPC-M 45.0 g

Eudragit RSPOL 50.0 g

The above starting materials were homogeneously mixed, granulated, dried, sieved and mixed with 1.3 g of magnesium stearate. The resulting mixture was made the shell which, together with the previously prepared core tablet, was compressed under a pressure of 1 ton with a press coating machine (Kikusui Cleanpress Correct 18DC), to provide press coated tablets containing 20 mg of nifedipine and weighing 295 mg per tablet (diameter=9 mm, thickness=5 mm). The tablets were further applied with the film coating same to that used in Example 1.

Example 4

Nifedipine 3.75 g (micropulverized crystals)

Lactose 26.05 g

HPC-L 20.0 g

The above starting materials were homogeneously mixed, granulated, dried, sieved and mixed with 0.2 g of magnesium stearate. The mixture was compressed under a pressure of 0.5 ton, with a single punch tableting machine (Korsch EKO), to provide the core tablets weighing 50 mg per tablet (diameter=5 mm, thickness=2 mm).

Nifedipine 6.25 g (micropulverized crystals)

HPC-L 147.45 g

HPC-M 45.0 g

Eudragit RSPOL 50.0 g

The above starting materials were homogeneously mixed, granulated, dried and sieved. The mixture was further mixed with 1.3 g of magnesium stearate. This composition was made the shell which, together with the previously prepared core tablets, compressed under a pressure of 1 ton with a press coating machine (Kikusui Cleanpress Correct 18DC) to provide press coated tablets containing 20 mg of nifedipine and weighing 300 mg per tablet (diameter=9 mm, thickness=5 mm). The tablets were further applied with the film coating same as that used in Example 1.

Comparative Example 1

Nifedipine 7.0 g (micropulverized crystals)

Lactose 15.0 g

Corn starch 17.85 g

Crosslinked polyvinylpyrrolidone 5.0 g

Crystalline cellulose 5.0 g

The above starting materials were homogeneously mixed, granulated, dried, sieved, and mixed with 0.15 g of magnesium stearate. The mixture was compressed under a pressure of 0.5 ton with a single punch tableting machine (Korsch EKO) to provide core tablets weighing 50 mg per tablet (diameter=5 mm, thickness=2 mm).

Nifedipine 33.0 g (micropulverized crystals)

HPC-L 110.0 g

HPC-M 70.0 g

Lactose 35.3 g

The above starting materials were homogeneously mixed, granulated, dried, sieved and mixed with 1.7 g of magnesium stearate. This composition was used as the coating (shell) which, together with the previously prepared core tablets, was compressed under a pressure of 1 ton with a press coating machine (Kikusui Cleanpress Correct 18DC) to provide press coated tablets containing 40 mg of nifedipine and weighing 300 mg per tablet (diameter=9 mm, thickness=5 mm). The tablets were further applied with the film coating same as that used in Example 1.

Comparative Example 2

Nifedipine 15.0 g (micropulverized crystals)

Lactose 10.0 g

Crosslinked polyvinylpyrrolidone 5.0 g

Crystalline cellulose 17.2 g

Polyvinylpyrrolidone 1.8 g

Polysorbate 80 0.8 g

The above starting materials were homogeneously mixed, granulated, dried, sieved and mixed with 0.2 g of magnesium stearate. This mixture was compressed to tablets under a pressure of 0.5 ton with a single punch tableting machine (Korsch EKO) to provide the core tablets weighing 50 mg per tablet (diameter=5 mm, thickness=2 mm).

Nifedipine 25.0 g (micropulverized crystals)

HPC-L 25.0 g

HPC-M 155.0 g

Lactose 44.0 g

The above starting materials were homogeneously mixed, granulated, dried, sieved and mixed with 1.0 g of magnesium stearate. This composition was used as the coating (shell) which, together with the previously prepared core tablets, was compressed under a pressure of 1 ton with a press coating machine (Kikusui Cleanpress Correct 18DC) to provide dry coated tablets containing 40 mg of nifedipine and weighing 300 mg per tablet (diameter=9 mm, thickness=5 mm). The tablets were further applied with the film coating same as that used in Example 1.

Comparative Example 3

Nifedipine 33.0 g (micropulverized crystals)

HPC-L 2.7 g

HPC-M 163.0 g

Eudragit RSPOL 50.0 g

The above starting materials were homogeneously mixed, granulated, dried, sieved and mixed with 1.3 g of magnesium stearate. This composition was used as the shell which, together with the core tablets as prepared in Example 1, was compressed under a pressure of 1 ton with a press coating machine (Kikusui Cleanpress Correct 18DC) to provide press coated tablets containing 40 mg of nifedipine and weighing 295 mg per tablet (diameter=9 mm, thickness=5 mm). The tablets were further applied with the film coating same as that used in Example 1.

Test Example

Each one of the tablets formed in Examples 1–2, Comparative Examples 1–3 and a commercial twice-a-day administration type sustained release nifedipine tablet (commercial name: Adalat L Tablet 20 mg; containing 20 mg of nifedipine) was orally administered to 12 healthy adult men single time at fasting state, and the nifedipine dynamics in blood of the subjects were compared. The results are indicated in Table 1.

TABLE 1

| Test tablet | Nifedipine Dynamics in Blood (average ± standard deviation) | |
|---|---|---|
|  | $C_{24}$* (ng/ml) | AUC (ng.hr/ml) |
| Example 1 | 12.4 ± 6.0 | 815.2 ± 424.0 |
| Example 2 | 12.6 ± 7.2 | 793.7 ± 382.8 |
| Comparative Example 1 | 7.9 ± 4.7 | 858.7 ± 391.4 |
| Comparative Example 2 | 7.1 ± 5.1 | 647.7 ± 452.5 |
| Comparative Example 3 | 5.6 ± 4.3 | 506.6 ± 286.2 |
| Adalat-L Tablet | 3.1 ± 2.0 | 391.5 ± 156.0 |

*Plasmic concentration of nifedipine after 24 hours from administration

The plasmic concentration of nifedipine after 24 hours from the administration of the tablets of Examples was higher than that after 12 hours from the administration of said commercial twice-a-day administration type sustained release nifedipine tablet. Thus, the tablets of Examples are expected to continuously exhibit the pharmacological effect for at least 24 hours per administration. Furthermore, it could be seen, when the inventive tablets were administered, that the maximum plasmic concentration of nifedipine was approximately equal to that of the commercial twice-a-day administration types sustained release nifedipine tablet.

Moreover, the area under the plasmic concentration curve for the tablets of Examples was approximately two times that for the commercial twice-a-day administration type sustained release nifedipine tablet, which confirms their excellent bioavailability.

In comparison to Comparative Examples, the inventive tablets show a higher plasmic concentration of nifedipine after 24 hours from administration.

Dissolution patterns of nifedipine from the press coated tablets prepared in Examples 1–2 and Comparative Examples 1–3, and that from the tablet of identical composition with that of the shell in Example 2 are shown in Table 2 and FIGS. 1 and 2.

TABLE 2

| Test tablet | Dissolution Rate of Nifedipine from Tablet (%) (average ± standard deviation) | | | | |
|---|---|---|---|---|---|
|  | Pharmacopoeia method 2 (using sinker) | | | Disintegration test device method | |
|  | 2 hrs. | 4 hrs. | 6 hrs. | 3 hrs. | 4 hrs. |
| Example 1 | 27.9 ± 0.8 | 54.9 ± 1.1 | 80.6 ± 4.5 | 37.3 ± 2.3 | 49.5 ± 3.8 |
| Example 2 | 26.4 ± 0.2 | 48.7 ± 0.4 | 90.5 ± 10.8 | 31.2 ± 1.6 | 43.3 ± 4.8 |
| Comparative Example 1 | 30.7 ± 0.1 | 78.2 ± 2.8 | 103.5 ± 1.0 | 95.1 ± 3.0 | 102.8 ± 1.1 |
| Comparative Example 2 | 12.1 ± 0.9 | 26.8 ± 1.1 | 46.9 ± 11.5 | 53.4 ± 17.4 | 76.6 ± 9.1 |
| Comparative Example 3 | 12.8 ± 0.3 | 28.7 ± 0.6 | 43.6 ± 1.0 | 18.6 ± 1.1 | 25.2 ± 1.2 |
| Tablet composed of shell of Example 2 | 36.8 ± 0.8 | 67.9 ± 1.1 | 89.5 ± 1.0 | 43.5 ± 1.4 | 55.9 ± 1.9 |

Dissolution patterns of nifedipine from the press coated tablets having identical compositions with those of the core tablets used in Examples 1 and 2 and Comparative Examples 1 and 2, respectively, were as indicated in Table 3.

TABLE 3

Dissolution Rate of Nifedipine from Core (%)
Pharmacopoeia method 2 dissolution test
(not using sinker)
(average ± standard deviation)

|  | 45 min. | 120 min. |
| --- | --- | --- |
| Example 1 | 44.2 ± 4.7 | 99.6 ± 3.3 |
| Example 2 | 49.8 ± 9.8 | 96.4 ± 0.8 |
| Comparative Example 1 | >75 |  |
| Comparative Example 2 | >75 |  |

Figure 1:
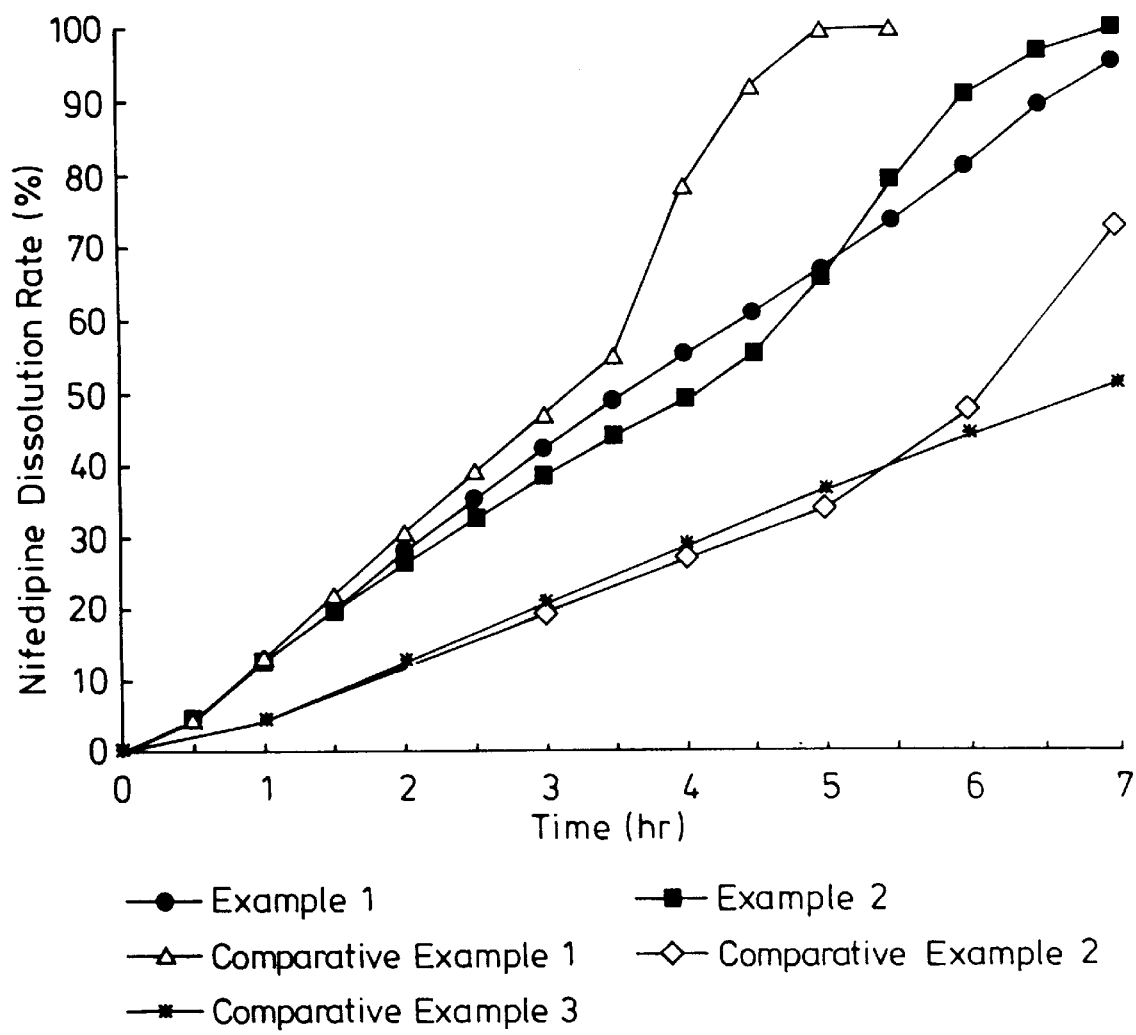
FIG. 1 shows the dissolution patterns of nifedipine from the tablets of Examples and Comparative Examples according to the Pharmacopoeia method 2 dissolution test (using sinker).
Figure 2:
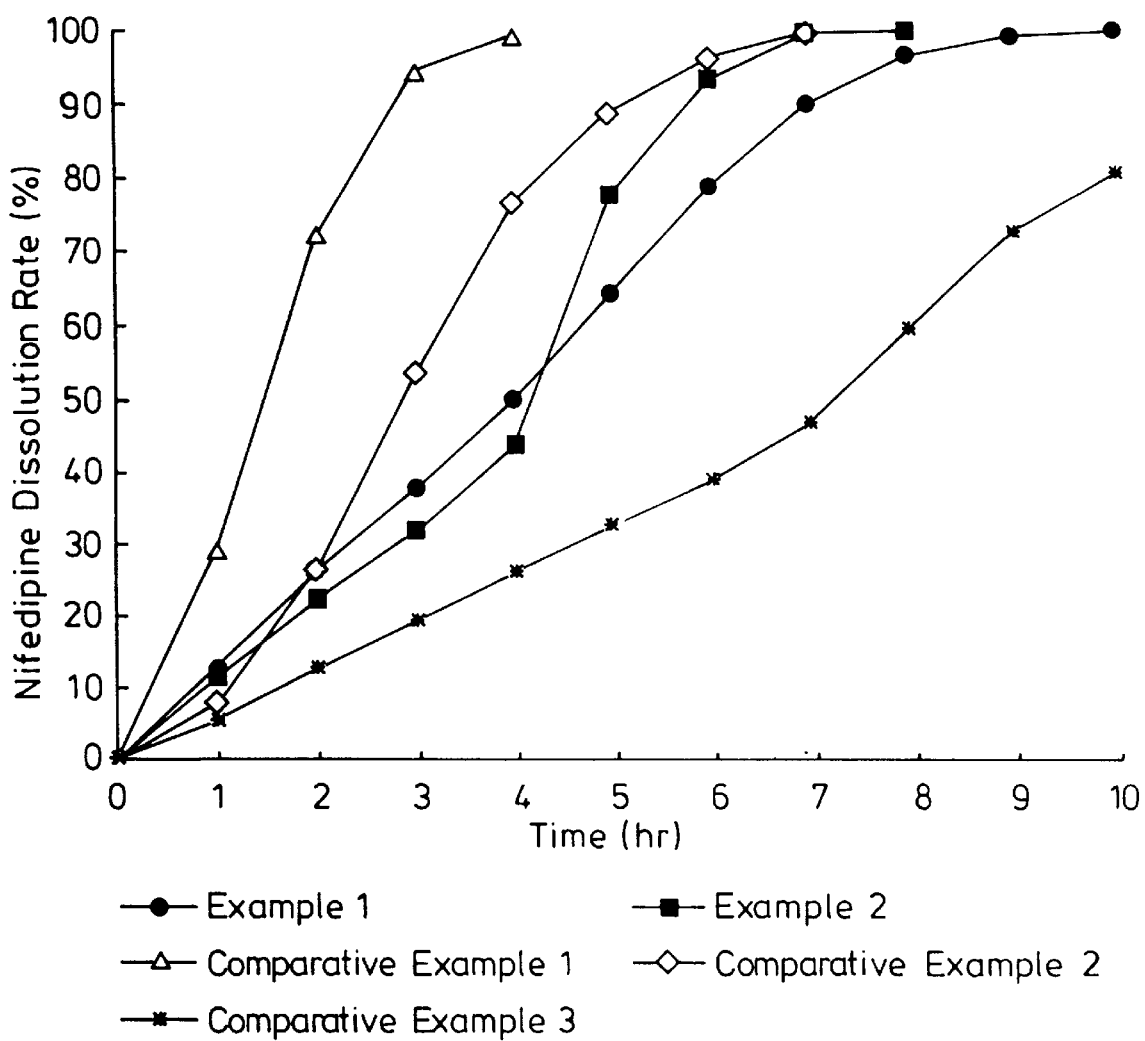
FIG. 2 shows the dissolution patterns of nifedipine from the tablets of Examples and Comparative Examples according to the Pharmacopoeia disintegration test device method.

We claim:

1. A nifedipine-containing press coated tablet which comprises a core containing nifedipine and hydrophilic gel-forming high molecular weight substance, and a shell which coats the core and which contains nifedipine, hydrophilic gel-forming high molecular weight substance and a disintegration suppression substance comprising at least one pH-independent water-insoluble polymer, which tablet is characterized in that the dissolution rate of the nifedipine from said tablet is:

(a) in the dissolution rate using a sinker according to method 2 of the dissolution test method as prescribed by the Pharmacopoeia of Japan,
      after 2 hours 10–40%
      after 4 hours 30–65%
      after 6 hours at least 55%, and (b) in the dissolution test according to the disintegration test method as prescribed by the Pharmacopoeia of Japan,
      after 3 hours 20–45%
      after 4 hours 30–65%.

2. A tablet according to in claim 1, in which the dissolution rate of the nifedipine from the tablet is:

(a) in the dissolution test using a sinker according to method 2 of the dissolution test method as prescribed by the Pharmacopoeia of Japan,
      after 2 hours 15–35%
      after 4 hours 35–60%
      after 6 hours at least 60%, and (b) in the dissolution test according to the disintegration test method as prescribed by the Pharmacopoeia of Japan,
      after 3 hours 25–40%
      after 4 hours 35–60%.

3. A tablet according to claim 1, in which the dissolution rate of the nifedipine from a tablet of identical composition with that of the core is:
   after 45 minutes 20–70%
   after 2 hours at least 65%,
when tested according to the method 2 of the dissolution test method not using a sinker, as prescribed by the Pharmacopoeia of Japan.

4. A tablet according to claim 1, in which the dissolution rate of the nifedipine from a tablet of identical composition with that of the shell is:

(a) in the dissolution test using a sinker according to method 2 of the dissolution test method as prescribed by the Pharmacopoeia of Japan,
      after 2 hours 20–50%
      after 4 hours 40–90%
      after 6 hours at least 75%, and (b) in the dissolution test according to the disintegration test method as prescribed by the Pharmacopoeia of Japan,
      after 3 hours 30–60%
      after 4 hours 40–90%.

5. A tablet according to claim 1, in which the core contains 5–90% by weight of hydrophilic gel-forming high molecular weight substance, and the shell contains 30–90% by weight of hydrophilic gel-forming high molecular weight substance and 5–50% by weight of disintegration suppression substance.

6. A tablet according to claim 5, in which the core contains 10–80% by weight of hydrophilic gel-forming high molecular weight substance and the shell contains 35–85% by weight of hydrophilic gel-forming high molecular weight substance and 7.5–40% by weight of disintegration suppression substance.

7. A tablet according to claim 5, in which the core contains 10–70% by weight of hydrophilic gel-forming high molecular weight substance and the shell contains 40–80% by weight of hydrophilic gel-forming high molecular weight substance and 10–30% by weight of disintegration suppression substance.

8. A method of treating hypertension in a patient suffering therefrom comprising administering to said patient a tablet according to claim 1.

9. A tablet as defined in claim 1, in which the hydrophilic gel-forming high molecular weight substance is a hydroxy lower alkyl ether of cellulose.

10. A nifedipine-containing press coated tablet which comprises a core containing nifedipine and hydrophilic gel-forming high molecular weight substance, and a shell which coats the core and which contains nifedipine, hydrophilic gel-forming high molecular weight substance and a disintegration suppression substance comprising at least one pH-independent water-insoluble polymer selected from the group consisting of poly ethyl acrylate, poly methyl methacrylate, and poly trimethylammonioethyl methacrylate chloride, which tablet is characterized in that the dissolution rate of the nifedipine from said tablet is:

(a) in the dissolution rate using a sinker according to method 2 of the dissolution test method as prescribed by the Pharmacopoeia of Japan,
      after 2 hours 10–40%
      after 4 hours 30–65%
      after 6 hours at least 55%, and (b) in the dissolution test according to the disintegration test method as prescribed by the Pharmacopoeia of Japan,
      after 3 hours 20–45%
      after 4 hours 30–65%.

11. A tablet according to claim 10, wherein the hydrophilic gel-forming high molecular weight substance is a hydroxy lower alkyl ether of cellulose.

12. A method of treating hypertension in a patient suffering therefrom comprising administering to said patient a tablet according to claim 10.

* * * * *